United States Patent [19]
Stein et al.

[11] 3,943,249
[45] Mar. 9, 1976

[54] O,O-DIETHYLTHIONOPHOSPHONYL-α-OXIMINO-5-CHLORO-2-THIENYL ACETONITRILE AS INSECTICIDES

[75] Inventors: Robert George Stein, Kenosha, Wis.; Aldo Joseph Crovetti, Lake Forest; Terry Lee Couch, Waukegan, both of Ill.

[73] Assignee: Abbott Laboratories, North Chicago, Ill.

[22] Filed: Sept. 20, 1973

[21] Appl. No.: 399,762

Related U.S. Application Data

[63] Continuation-in-part of Ser. No. 215,957, Dec. 20, 1971, abandoned.

[52] U.S. Cl. .............................................. 424/202
[51] Int. Cl.$^2$ ........................................... A01N 9/36
[58] Field of Search ..................................... 424/202

[56] References Cited

UNITED STATES PATENTS 2,957,007 10/1960 McCall et al. .................. 260/332.5
3,106,566 10/1963 McCall et al. .................. 260/332.5
3,462,439 4/1969 Popoff et al. ....................... 260/290
3,469,004 9/1969 Kaufman et al. ................... 424/202
3,567,803 3/1971 Ward et al. ......................... 260/972
3,591,662 7/1971 Lorenz et al. ....................... 260/940
3,634,557 1/1972 Hubele ............................... 260/944
3,639,537 2/1972 Kaufman ............................ 260/940
3,652,741 3/1972 Montgomery et al. ............ 260/956

FOREIGN PATENTS OR APPLICATIONS 530,166 12/1972 Switzerland

*Primary Examiner*—Sam Rosen
*Assistant Examiner*—D. W. Robinson
*Attorney, Agent, or Firm*—Robert L. Niblack; James L. Bailey; Vincent A. Mallare

[57] ABSTRACT

The invention covers the use of O,O-diethylthionophosphonyl-α-oximino-5-chloro-2-thienyl acetonitrile as a pesticide.

8 Claims, No Drawings

O,O-DIETHYLTHIONOPHOSPHONYL-<-OXIMINO-5-CHLORO-2-THIENYL ACETONITRILE AS INSECTICIDES

REFERENCE TO RELATED APPLICATION

This application is a continuation-in-part application of copending application filed Dec. 20, 1971, bearing Ser. No. 215,957, now abandoned.

SUMMARY OF THE INVENTION

This invention relates to O,O-diethylthionophos-phonyl-α-oximino-5-chloro-2-thienyl acetonitrile and its use for controlling insects and acarid pests and to new pesticidal formulations comprising O,O-diethylthionophosphonyl-α-oximino-5-chloro-2-thienyl acetonitrile as an essential active ingredient in combination with various diluent carriers.

DETAILED DESCRIPTION OF THE INVENTION

O,O-diethylthionophosphonyl-α-oximino-5-chloro-2-thienyl acetonitrile may be prepared by a variety of methods. However, it is most conveniently prepared as follows:

A solution of 11.3 g. (0.06 mole) of diethyl chlorothiophosphate was added dropwise to a stirred solution of 11.16 g. (0.06 mole) of α-oximino-5-chloro-2-thienyl acetonitrile and 6.06 (0.06 mole) of triethylamine in 200 ml. of diethyl ether. The mixture was stirred four hours and successively washed with water, dilute sodium hydroxide solution and water. The solution was dried over magnesium sulfate, filtered and concentrated to an oil. Upon standing the oil was induced to crystallize. A recrystallization from pentane gave a pure material which melted at 46° – 47° C.

The compound had the following structural formula:

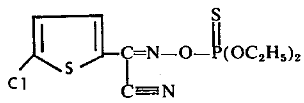

and analyzed as follows:

Calcd: C: 35.45, H: 3.56, N: 8.26;

Found: C: 36.19, H: 3.69, N: 8.21.

Advantageously, O,O-diethylthionophosphonyl-α-oximino-5-chloro-2thienyl acetonitrile, hereinafter referred to as the "compound" exhibits strong insecticidal and acaricidal activities, with comparatively low toxicity to warm-blooded animals and concomitently low phytotoxicity. The effects set in rapidly and are long lasting. The instant active compound can therefore be used with favorable results for the control of noxious sucking and biting insects, Diptera and mites (Acarina).

Among the insects which can be effectively controlled by the compound of the present invention are the chewing insects such as the Mexican bean beetle, and the southern armyworm; the piercing-sucking insects, such as the pea aphid, the cereal leaf beetle, the housefly, the grape leafhopper, the chinch bug, the lygus bugs, oyster shell scale, the California red scale, the Florida red scale, the soft scale and mosquitoes; the internal feeders, including borers such as the European corn borer, the peach twig borer and the corn earworm; worms or weevils such as the codling moth, alfalfa weevil, cotton boll weevil, pink boll worm, plum curculio, red band leaf roller, melon worm, cabbage looper, and apple maggott; leafminers such as the apple leaf miner, birch miner and beet leaf miner; and gall insects such as the wheat joint worm and the grape phylloxera. Insects which attack below the surface of the ground are classified as subterranean insects and include such destructive pests as the woolly apple aphid, the Japanese beetle, the onion maggott and the corn root worm.

Mites and ticks are not true insects. Many economically important species of mites and ticks can be controlled by the compound of this present invention such as the red spider mite, the two spotted spider mite, the strawberry spider mite, the citrus red mite and the European red mite. Chemicals useful for the control of mites are often called miticides while those useful for the control of both mites and ticks are known specifically as acaricides.

The new compound of this invention can be used in many ways for the control of insects or acarids. Insecticides or acaricides which are to be used as stomach poisons or protective materials can be applied to the surface on which the insects or acarids feed or travel. Insecticides or acarcides which are to be used as contact poisons or eradicants can be applied directly to the body of the insect or acarid, as a residual treatment to the surface on which the insect or acarid may walk or crawl, or as a fumigant treatment of the air which the insect or acarid breathes. In some cases, the compound applied to the soil or plant surfaces is taken up by the plant, and the insects or acarids are poisoned systemically. In essence then, the just-described methods of using the insecticide or acaricide here are based on the fact that almost all the injury done by insects or acarids is a direct or indirect result of their attempts to secure food.

The active compound according to the instant invention can be utilized, if desired, in the form of the usual formulations or compositions with conventional inert pesticidal diluents or extenders, i.e. conventional pesticidal dispersible carrier vehicles, such as solutions, emulsions, suspensions, emulsifiable concentrates, spray powders, pastes, soluble powders, dusting agents, granules, etc. These are prepared in known manners, for instance by extending the active compound with conventional pesticidal dispersable liquid diluent carriers and/or dispersible solid carriers, optionally with the use of carrier vehicle assistants, e.g. conventional pesticidal surface-active agents, including emulsifying agents, dispersing agents, whereby, for example, in the case where water is used as a diluent, organic solvents may be added as auxiliary solvents. The following may be chiefly considered for use as conventional carrier vehicles for this purpose: inert dispersible liquid diluent carriers, including inert organic solvents such as aromatic hydrocarbons (e.g. benzene, toluene, xylene, etc.), halogenated, especially chlorinated, aromatic hydrocarbons (e.g. chlorobenzenes, etc.), paraffins (e.g. petroleum fractions), chlorinated aliphatic hydrocarbons (e.g. methylene chloride, etc.), alcohols (e.g. methanol, ethanol, propanol, butanol, etc.), amines (e.g. ethanol amine, etc.), ethers, ether-alcohols (e.g. glycol monomethyl ether, etc.), amides (e.g. dimethylformamide, etc.), sulfoxides (e.g. dimethyl sulfoxide, etc.), ketones (e.g. acetone, etc.), and/or water; as well as inert dispersible finely divided solid carriers such as ground natural minerals (e.g. kalines, alumina, silica, chalk)(i.e. calcium carbonate, talc, kieselguhr, etc), and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose; emulsifying agents, such as nonionic and/or anionic emulsifying agents (e.g. polyethylene oxide esters of fatty acids, polyethylene oxide ethers of fatty alcohols, alkyl sulfonates, aryl sulfonates, etc. and especially alkyl arylpolyglycol ethers, magnesium stearate, sodium oleate, etc.); and/or dispersing agents, such as lignin, sulfite waste liquors, methyl cellulose, etc.

The active compound of the invention may be employed with other known compatable active agents, especially plant protection agents, such as other acaricides, insecticides, molluscicides, nematicides, fungicides, herbicides, bactericides, etc. if desired, or in the form of particular dosage preparations for specific application made therefrom, such as solutions, emulsions, suspensions, powders, pastes and granules which are thus ready for use.

Typical insecticides or acaricides with which the compound of the invention can be used in the insecticidal or acaricidal compositions to control insects or acarids include halogenated compounds such as DDt, methoxychlor, TDE, lindane, chlordane, isobenzan, aldrin, dieldrin, hepthchlor, endrin, mirex, endosulfon, dicofol, and the like; organic phosphorus compounds such as TEPP, schradan, ethion, parathion, methyl parathion, EPN, demeton, carbonphenothion, phorate, zinophos, diazinon, malathion, mevinphos, dimethoate, DBD, ronnel oxydemeton-methyl, dicapthon, chlorothion phosphamidon, naled fenthion, trichorofon, DDVP, and the like; organic nitrogen compounds such as dinitro-o-cresol, dinitrocyclohexylphenol, DNB, DNP, binapacril, azobenzene, and the like; organic carbamate compounds, such as carbaryl and the like; organic sulfur compounds such as phenothiazine, phenoxathin, lauryl thiocyante, bis(2-thiocyanoethyl)ether, isobornyl thiocyanoacetate, and the like; as well as such substances usually referred to as fumigants, as hydrogen cyanide, carbon tetrachloride, calcium cyanide, carbon disulfide, ethylene dichloride, propylene dichloride, ethylene dibromide, ethylene oxide, methyl bromide, paradichlorobenzene, and the like.

As concerns commercially-marketed preparations, these generally contemplate carrier composition mixtures in which the active compound is present in an amount substantially between 0.1 – 95% by weight, and preferably 0.5 – 90% by weight of the mixture, whereas carrier composition mixtures suitable for direct application or field application generally contemplates those in which the active compound is present in an amount substantially between 0.00001 – 20%, preferably 0.0002 – 20%, and most preferably 0.01 –2% by weight of the mixture. Thus, the present invention contemplates over all compositions which comprise mixtures of the conventional dispersible carrier vehicle such as (1) a dispersible inert finely divided solid, and/or (2) a dispersible carrier liquid such as an inert organic solid and/or water, preferably including a surface-active effective amount of a carrier vehicle assistant, e.g. a surface-active agent, such as an emulsifying agent and/or a dispersing agent, and an amount of the active compound which is effective for the purpose in question which is generally between about 0.00001 – 95% and preferably 0.01 – 95%.

The compound here was tested as to its insecticidal activity utilizing as test insects the housefly (*Musca domestica* Linnaeus), the two-spotted spider mite (*Tetranychus urticae*) and the beet armyworm (*Spodoptera exigus*) and in each instance the compound was tested at a number of varying dosages. The ratings are as follows: VA indicates greater than 80% kill; A indicates a 50 – 80% kill; SLA indicates 25 – 49% kill; and I indicates a 0 – 25% kill.

In more detail, the following test precedures were used to screen the insecticide of the invention: With respect to the test on the housefly, three day old adult houseflies are used. Approximately 50 flies are used for each dilution of the chemical tested. Flies are anesthetized with carbon dioxide and placed in a Buchner funnel The appropriate dilution is then poured onto the flies. Contact time is approximately 5 seconds. The chemical is then removed by suction and the flies are transferred to glass beakers and mortality noted after one hour.

With respect to the spider mite, a leaf disc bioassay procedure is used to determine the miticidal activity of the compound of the invention. Specifically, leaf discs approximately 15 mm. in diameter cut from fresh Henderson Bush Lima Bean plants. The discs are then dipped in the appropriate dilution of the chemical. The leaf discs are allowed to dry and are then placed on moistened filter paper and appropriate labeled petri dishes. Ten adult mites are placed on each disc. Nine discs are used for each compound. Percent mortality is then determined after 48 hours.

The immersion technique described for the housefly was modified and used for the beet armyworm. Five to 7 day old larvae of *S. exigua* are immersed in the appropriare dilution of the insecticide for five seconds. The chemical is removed by suction and the worms are placed in petri dishes. Twenty four hours later mortality is determined.

Results of insecticidal activity are given in Tables I, II and III.

TABLE I

| Two-Spotted Spider Mite | | | | | | |
|---|---|---|---|---|---|---|
| 2500 ppm | 500 ppm | 250 ppm | 125 ppm | 30 ppm | 15 ppm | 5 ppm |
| VA | VA | VA | VA | VA | VA | SLA |

TABLE II

| Housefly | | | | | |
|---|---|---|---|---|---|
| 5000 ppm | 500 ppm | 250 ppm | 125 ppm | 62.5 ppm | 30 ppm |
| VA | VA | VA | VA | A | SLA |

TABLE III

| Beet Armyworm | | |
|---|---|---|
| 5000 ppm | 500 ppm | 250 ppm |
| VA | A | I |

It was surprising to note that a great number of analogs and homologs of the compound have had measurably less activity as insecticides and acaracides, such as against the species tested against above. The O,O-diethylthiono-phosphonyl-α-oximino-5-chloro-2-thienyl acetonitrile compound appears to be unique in its degree of activity.

We claim:

1. A method of controlling insects and mites which comprises contacting such insects and mites with an insecticidally effective amount of O,O-diethylthionophosphonyl-α-oximino-5-chloro-2-thienyl acetonitrile.

2. A pesticidal composition comprising an insecticidally effective amount of O,O-diethyl-thionophosphonyl-α-oximino-5-chloro-2-thienyl acetonitrile. and a pesticide diluent.

3. The pesticidal composition of claim 2 wherein said pesticide diluent is a solid.

4. The pesticidal composition of claim 3 wherein the solid pesticide diluent is in powder form.

5. The pesticidal composition of claim 3 wherein the solid pesticide diluent is in granular form.

6. The pesticidal composition of claim 2 wherein the pesticide diluent is a liquid.

7. The pesticidal composition of claim 6 wherein said liquid is water.

8. The pesticidal composition of claim 2 comprising from 0.00001% to 95% by weight of the active ingredient.

* * * * *